US005796106A

United States Patent [19]

Noack

[11] Patent Number: 5,796,106

[45] Date of Patent: Aug. 18, 1998

[54] ICE AND LIQUID DETECTOR

[76] Inventor: Raymond James Noack, P.O. Box 898, Springwood, Queensland, 4127, Australia

[21] Appl. No.: 765,236

[22] PCT Filed: Jun. 13, 1995

[86] PCT No.: PCT/AU95/00345

§ 371 Date: Dec. 18, 1996

§ 102(e) Date: Dec. 18, 1996

[87] PCT Pub. No.: WO95/35493

PCT Pub. Date: Dec. 28, 1995

[30] Foreign Application Priority Data

Jun. 20, 1994 [AU] Australia .............................. PM 6319

[51] Int. Cl.$^6$ .......................... G01N 21/88; G01N 21/01

[52] U.S. Cl. ...................................... 250/341.8; 250/341.1; 15/DIG. 15

[58] Field of Search .............................. 250/341.1, 341.8, 250/339.11; 15/DIG. 15

[56] References Cited

U.S. PATENT DOCUMENTS

| | | | |
|---|---|---|---|
| 3,947,131 | 3/1976 | Karl | 250/341.8 X |
| 4,620,141 | 10/1986 | McCumber et al. | 15/DIG. 15 X |
| 5,414,257 | 5/1995 | Stanton | 250/341.8 X |

FOREIGN PATENT DOCUMENTS

| | | | |
|---|---|---|---|
| 4312590 | 10/1993 | Germany | 250/341.8 |

*Primary Examiner*—Edward J. Glick

*Attorney, Agent, or Firm*—Mathews, Collins, Shepherd & Gould, P.A.

[57] ABSTRACT

A detector for detecting the presence of ice, water, mist, frost or other solids or liquids on a sensing surface is provided. The sensing surface is provided by a medium substantially transparent to electromagnetic radiation and solids or liquids are deposited on the surface. A transmitter directs radiation onto the surface and a receiver is responsive to radiation reflected from the surface. A discriminator circuit receivers an output from the receiver and provides an output indicative of whether a solid or a liquid is present on the surface.

9 Claims, 4 Drawing Sheets

I-R SENSOR RESPONSE TO SOLIDS AND LIQUIDS

ICE AND LIQUID DETECTOR

This invention concerns a detector for detecting the build up of water, frost or ice on a surface.

BACKGROUND OF THE INVENTION

The invention will be described by way of example with reference to use of the device to detect frost or ice formation within a refrigerator to control a defrost cycle in such a refrigerator. It should be appreciated that this is by way of example only and that the device of the invention may also be used in other applications. For example the device of the invention may be employed in detecting the formation of ice on windows, windscreens, aircraft wings and in controlling de-icing.

In no frost or frost free refrigerators a defrost cycle is periodically initiated to defrost the refrigerator to eliminate or minimise the build up of ice. Manufacturers of refrigerators currently determine defrost cycles for refrigerators by conducting tests in particular hot and humid climates and as a result of those tests preset defrost cycle requirements for refrigerators for all climatic conditions up to and including the conditions experienced at the test locality. This means that for locations where climatic conditions are not as severe, defrosting occurs more often than necessary and energy is wasted.

Timed defrost cycles are employed where a heating element of a capacity of about 500 W is energised for twenty-five minutes at a time about two or three times per day. Thus defrosting occurs regardless of whether there is any frost or ice build up in the refrigerator. It is desirable to complete the defrost cycle as quickly as possible so that the effects that opening of the refrigerator door have on the defrost cycle are minimised. Thus, a particularly large power capacity heating coil is employed to achieve defrosting.

No attempt is presently made to detect the presence of frost or ice and to initiate a defrost cycle only when frost or ice is present. Rather, heating to effect defrosting occurs for set time periods and a set number of times per day.

It is an object of the present invention to provide a detector which may be used to control a defrost cycle in a refrigerator which at least minimises the disadvantages referred to above.

DISCLOSURE OF THE INVENTION

According to one aspect, the invention provides a detector for detecting the presence of ice, water, frost or other solids and discriminating between the presence of solids and liquids, the detector including: a sensing surface provided by a medium substantially transparent to electromagnetic radiation and upon which solids or liquids may be deposited, a radiation transmitter for directing radiation onto the medium from a side of the medium opposed to the sensing surface, a radiation receiver receiving radiation reflected from the surface and a discriminator circuit operable in response to an output from the receiver to discriminate between the presence of liquids or solids on the surface and providing an output indicative of whether a solid or a liquid is present on the surface.

The electromagnetic radiation may be visible light, Infra-Red, Ultra-Violet or any other suitable radiation. Preferably Infra-Red radiation of a wavelength of 930 nm is employed. Where I-R radiation is used, the transmitter may comprise an I-R diode and the receiver an I-R photo transistor. Preferably, a reflective switch such as that manufactured by Honeywell and identified by the device code HOA-1397-2 or equivalent or substitute is used.

The medium which provides the sensing surface, as mentioned, is substantially transparent to the radiation employed. Glass or a plastics material such as acrylic or perspex may be used. Preferably glass is used. The sensing surface may be a partial mirror surface or a clear surface. Alternatively, the surface is frosted, patterned, grooved (dimples or ripples) or sandblasted or may be a combination of clear and frosted, patterned, grooved or sandblasted surface finishes. A normally clear surface allows most of the radiation impinging upon it to pass through and reflects only a small percentage of incident radiation. The presence of solids such as frost or ice on the surface causes the percentage of reflected radiation to increase while the presence of a liquid causes the percentage of reflected radiation to decrease.

Frosted, patterned or sandblasted surfaces or the like minimise the effects of reflections from objects close to the surface and assist in diffusing strong ambient light. The degree of frosting, patterning or the like on the surface may be controlled by sandblasting discrete dots, lines or grooves or cross-hatched lines or grooves onto the sensing surface.

Where I-R radiation is employed, it is preferred that the transmitter be pulsed to minimise heating of the medium. Preferably an oscillator is used to energise the transmitter. An oscillator which causes 50 μs pulses at 10 ms intervals may be used.

The medium is attached to the transmitter/receiver. Bonding of the transmitter/receiver to the medium is preferred. The bonding agent is preferably substantially transparent to the radiation. It is preferred that a clear silicon rubber material be used for this purpose.

The discriminator circuit receives an output from the I-R receiver and preferably has two circuit paths. One path determines an output indicative of the presence of a liquid on the sensing surface while the other path determines an output indicative of the presence of a solid such as ice or frost on the sensing surface.

The one path preferably includes an amplifier for amplifying the output received from the receiver. A gain of about 10 is preferred. An operational amplifier is preferred. The one path includes a converter for converting the pulsed output from the amplifier into a DC level indicative of the magnitude of the pulsed output from the receiver. An integrator or peak detector may be used for this purpose. The one path preferably includes a comparator for comparing the DC level with a reference potential. The comparator provides an output indicative of the presence of a liquid.

The other path preferably includes a converter for converting the pulsed output from the receiver into a DC level whose magnitude is indicative of the magnitude of the pulsed output from the receiver. An integrator or peak detector may be used. The other path preferably includes a comparator which provides an output indicative of the presence of solids such as frost or ice on the sensing surface. This output may be used to initiate a defrost cycle in a refrigerator with which the detector of the invention is associated. This comparator preferably is latched on to provide the indication of the presence of solids until the presence of liquid is indicated by the comparator in the one path. When that occurs it is preferred that the comparator be unlatched by the output from the comparator in the one path.

DISCLOSURE OF THE DRAWINGS

A particular preferred embodiment of the invention will now be described with reference to the drawings in which:

FIGS. 1 to 3 are views of possible ways in which an infra red emitter/receiver may be associated with a surface upon which frost may build up;

FIG. 4 is a graph useful in aiding the understanding of how the surface may be optimised to enable discrimination between the presence of solids and liquids; and FIG. 5 is a circuit diagram of a detector according to a preferred embodiment of the invention FIG. 5A shows an inset enlarged view of a portion of FIG. 5; and, FIG. 6 shows a detailed view of the emitter/receiver sandwiched between two sheets or laminates of glass.

DETAILED DESCRIPTION OF THE DRAWINGS

Figure 1:
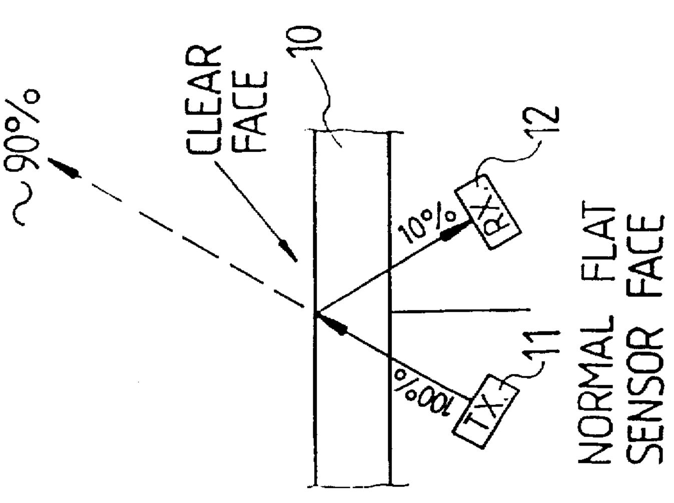

Electromagnetic radiation including Infra-Red radiation, visible light and Ultra-Violet radiation is absorbed by liquids and reflected by solids. A normally clear glass sheet allows most, typically about 90%, of the radiation to pass through reflecting a small amount, typically about 10%. FIG. 1 shows a clear sheet of glass 10, a transmitter 11 and a receiver 12. The angle of incidence may typically be about 10° to 30° although this is not crucial. Solids such as ice or frost on the exterior of the glass sheet cause more radiation to be reflected while the presence of liquid causes a decrease in reflection of radiation.

Figure 4:
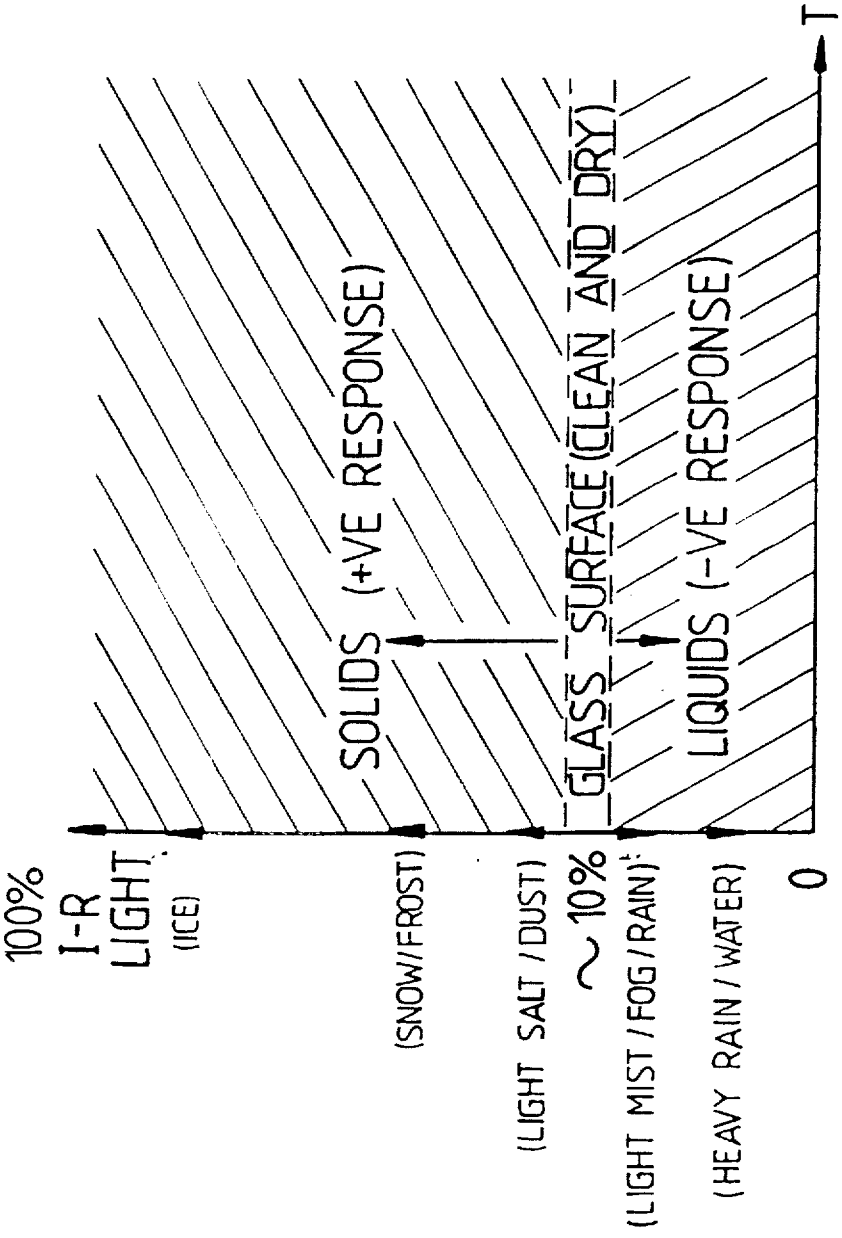

A frosted, patterned or grooved (dimples or ripples) exterior surface on the glass may increase the reflected radiation from about 10% to 50% to enhance discrimination between solids and liquids. By treating the surface of the glass in these ways the response graph as shown in FIG. 4 may be altered to have the "clean and dry" glass surface response at about 50% reflectivity and this is preferable.

Figure 2:
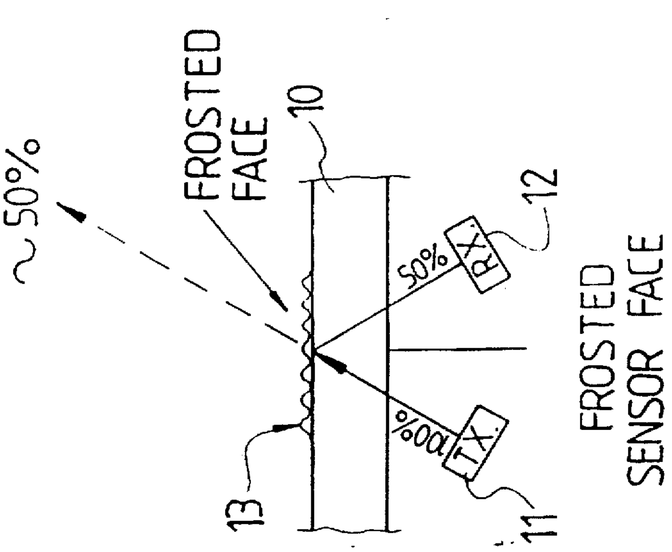
Figure 3:
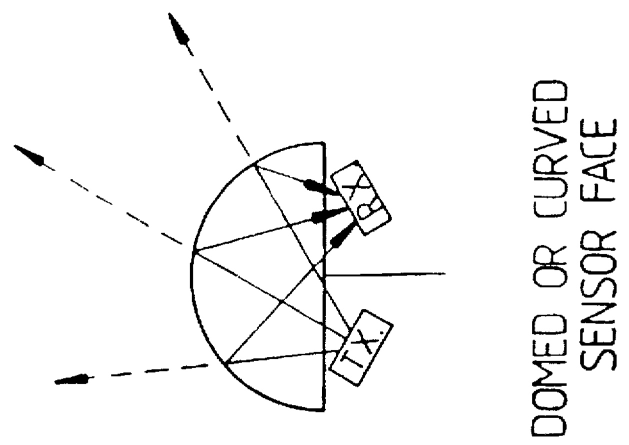

FIG. 2 shows a view much like FIG. 1 except the surface of the glass sheet 10 is frosted as shown at 13. The glass sheet need not be planar and FIG. 3 shows the reflective surface onto which the radiation is directed to be curved.

The transmitter/receiver of the invention may be sandwiched between two mediums with one of the mediums providing the surface on which frost, mist or ice is likely to form. For example, the one medium may be one laminate of a laminated vehicle windscreen. The one medium may still be treated to optimise discrimination. Thus a small area of the one laminate may be sandblasted for example. This is particularly advantageous for laminated windscreens or mirrors.

Figures 5, 5A:
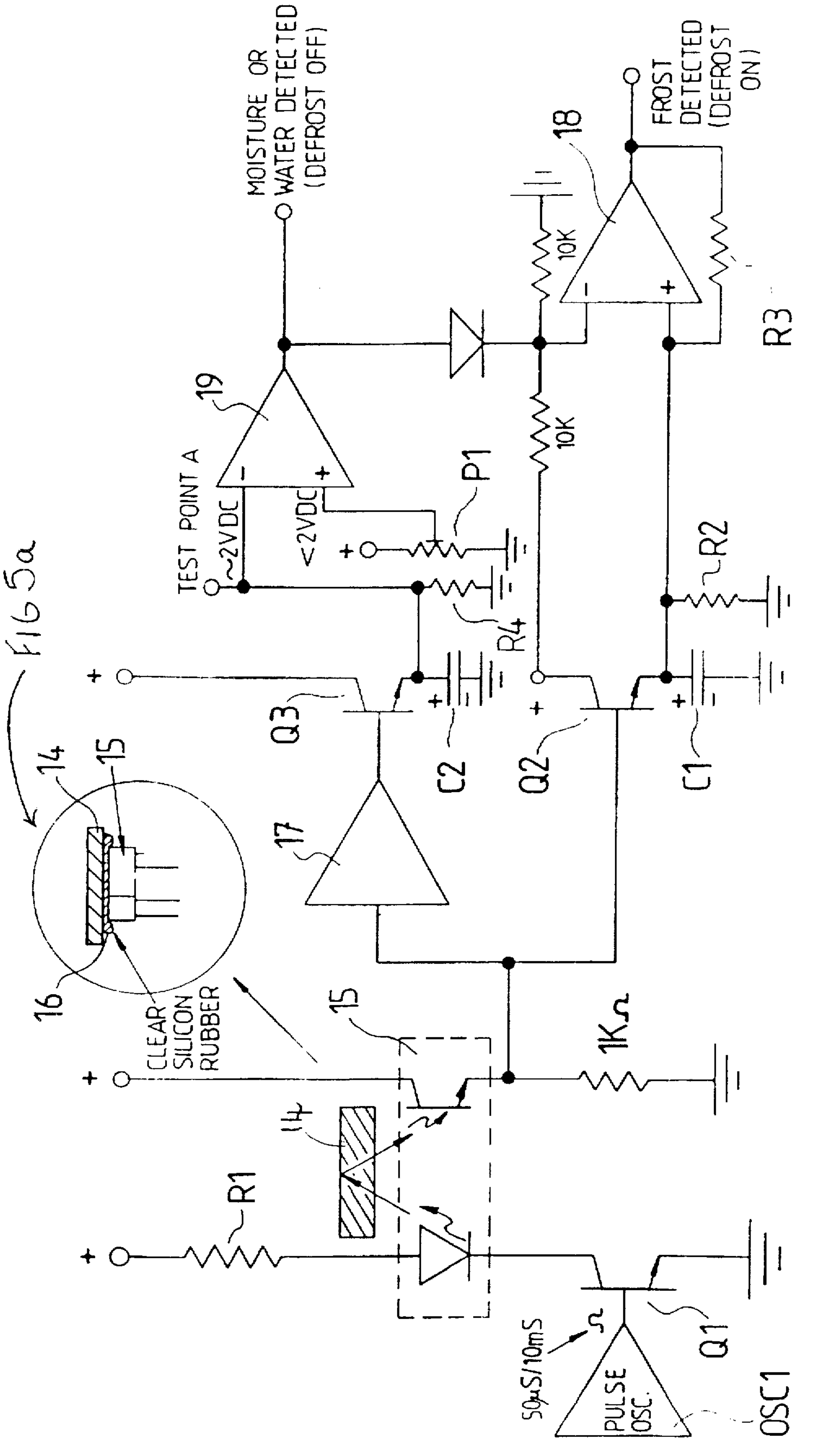

FIG. 5 shows a circuit diagram of a detector according to an embodiment of the invention. The inset view shows a sheet of glass 14 to which the radiation transmitter/receiver 15 is bonded by a bonding agent such as clear silicone rubber compound 16, as shown in FIG. 5A. The transmitter/receiver 15 may comprise a Honeywell device HOA-1397-2 Infra-Red emitter and receiver or equivalent.

The transmitter diode is connected in series with resistor R1 and the collector emitter path of transistor Q1. By pulsing transistor Q1 with 50 μs pulses every 10 ms with oscillator OSC1 there is no danger of the Infra-Red radiation directed onto the glass causing sufficient heating to melt any build up of ice on the exterior surface of the glass. A pulsed output is obtained from the transmitter/receiver 15 and applied to amplifier 17 and transistor Q2. The transistor Q2 has a capacitor C1 and resistor R2 coupled in parallel between the emitter and a reference potential (earth) and functions as a peak detector or integrator. The output from transistor Q2 is a DC level whose magnitude is proportional to the amount of radiation reflected from the glass 14. This signal is applied to the positive input of comparator 18. Comparator 18 has a feedback resistor R3 which ensures that the comparator is latched on when the magnitude of the positive input is greater than the negative input. This would be the case when solids such as frost or ice are present on the glass 14.

The signal applied to amplifier 17 is amplified and coupled to transistor Q3 which, with resistor R4 and capacitor C2 also functions as a peak detector or integrator. A DC level is available at the emitter of transistor Q3 which is indicative of reflected radiation detected by the receiver in transmitter/receiver 15 and typically is less than 2VDC when liquid is present on the glass and greater than this when solids are present. This DC level is applied to the negative input of comparator 19. A DC signal of about 1.5 to 2VDC is applied to the positive input of comparator 19 via potentiometer P1. The output of comparator 19 is low when solids are detected. When liquids are detected the output of comparator 19 is high. This high output is coupled to the negative input of comparator 18 and causes the comparator 18 to be unlatched and the output of comparator 18 becomes low again.

Thus, the presence of ice or frost on the glass produces a high signal at the output of the comparator 18 which may be used to commence a defrost cycle in a refrigerator. The output at comparator 19 is low when frost or ice is detected and becomes high when liquid is detected. If desired, that output may be used to indicate that a defrost cycle has been completed or that moisture has been detected.

Figure 6:
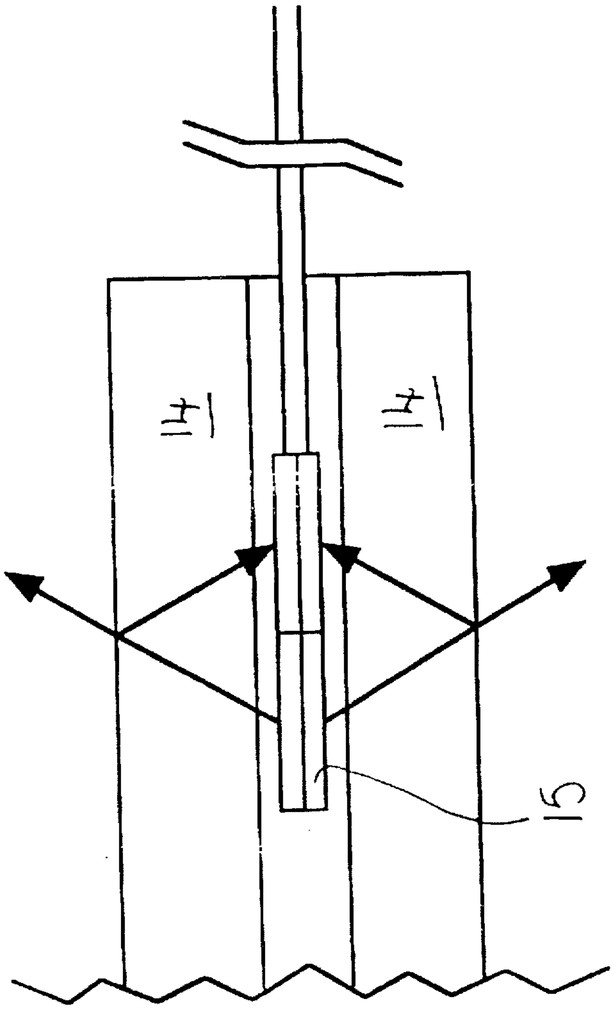
Figures 5, 5A:
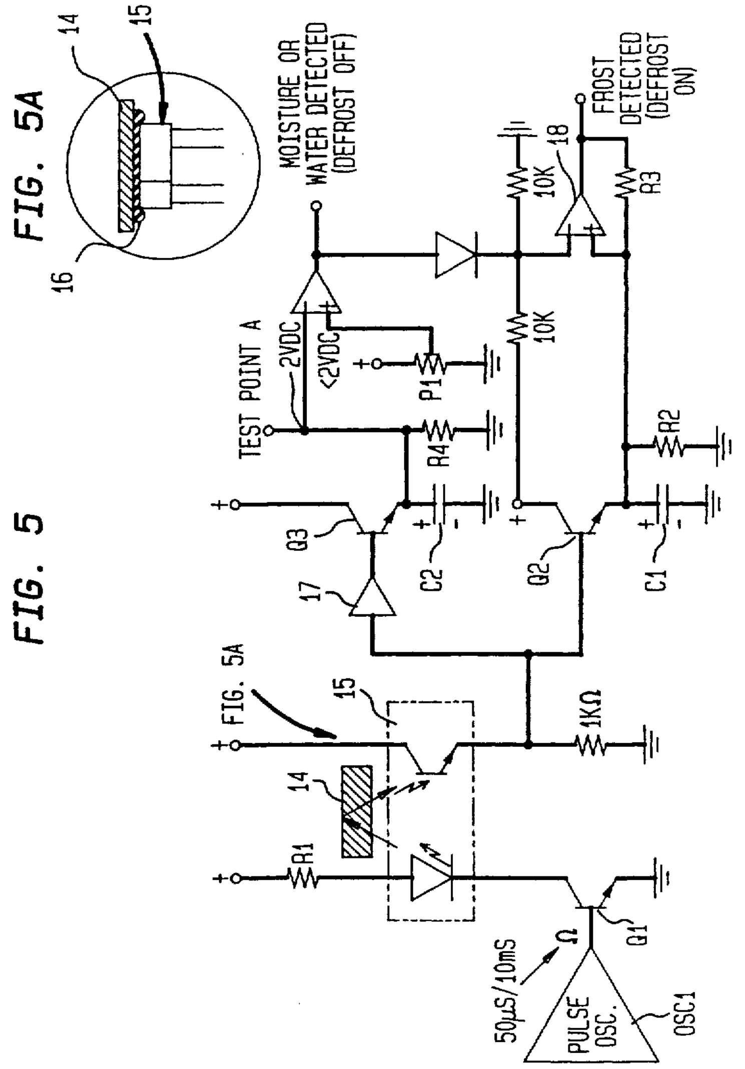

With the detector of the invention a defrost cycle may be initiated only when necessary and once initiated defrost heating will only continue until defrosting has been achieved. FIG. 6 shows transmitter/receiver 15 between two sheets of glass 14.

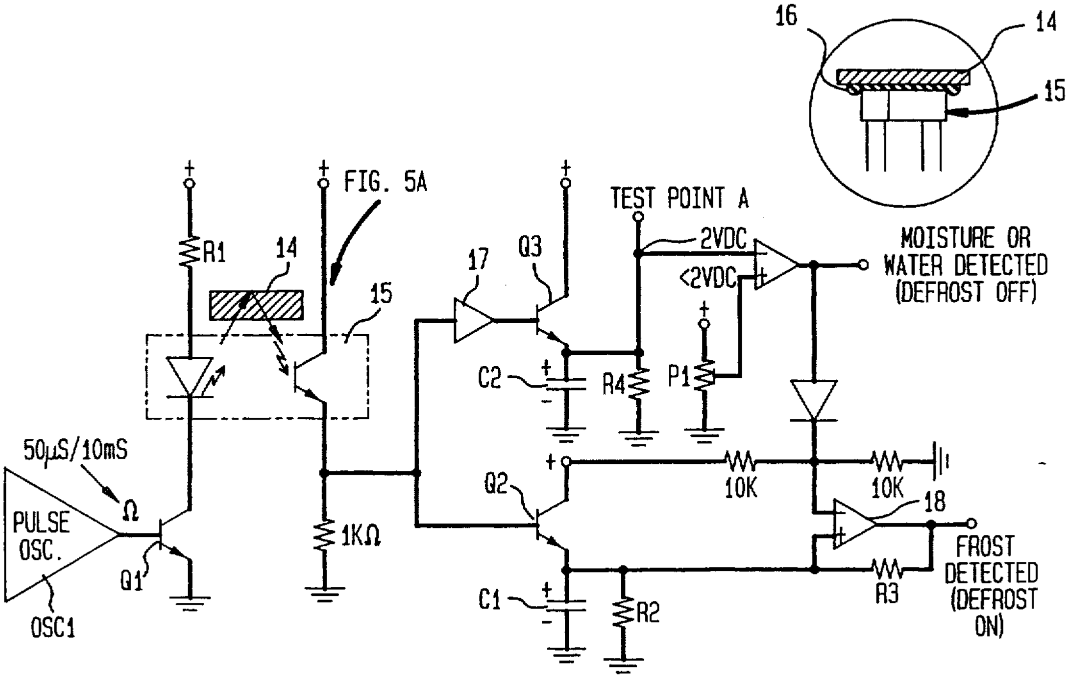

I claim:

1. A detector for detecting the presence of liquids or solids and discriminating between the presence of the solids and the liquids, the detector comprising: a sensing surface provided by a medium substantially transparent to electromagnetic radiation and upon which the solids or the liquids may be deposited, the sensing surface being patterned, grooved, dimpled, rippled, sandblasted or etched, a radiation transmitter for directing radiation onto the medium from a side of the medium opposed to the sensing surface, a radiation receiver receiving radiation reflected from the surface and a discriminator circuit operable in response to an output from the receiver to discriminate between the presence of the liquids or the solids on the surface and providing an output indicative of whether a solid or a liquid is present on the surface, the receiver and the transmitter both being bonded to the medium.

2. The detector of claim 1 wherein the electromagnetic radiation is Infra-Red radiation.

3. The detector of claim 1 wherein the medium is glass.

4. The detector of claim 3 wherein the glass medium provides a first laminate of a two laminate glass windscreen of a vehicle and the transmitter and the receiver are sandwiched between the two laminates.

5. The detector of claim 1 wherein the discriminator has a first circuit path for providing an output indicative of the presence of a liquid on the sensing surface and a second circuit path for providing an output indicative of the presence of a solid on the sensing surface.

6. The detector of claim 5 wherein the first circuit path includes an amplifier for amplifying the output from the receiver and a converter for converting an output from the amplifier into a DC voltage level indicative of the magnitude of the receiver output.

7. The detector of claim 6 wherein the first path includes a comparator for comparing the DC level with a reference potential and wherein the comparator provides an output indicative of the presence of a liquid on the sensing surface.

8. The detector of claim 7 wherein the second circuit path includes a second converter for converting the output from the receiver into a DC voltage level and a comparator which receives the output from the second converter and the output indicative of the presence of a liquid and provides an output indicative of solids on the sensing surface.

9. The detector of claim 8 wherein the output from the comparator in the second circuit path is latched on to provide the indication of the presence of solids on the sensing surface and is unlatched by the liquid indicative output from the comparator in the first circuit path.

* * * * *

UNITED STATES PATENT AND TRADEMARK OFFICE
CERTIFICATE OF CORRECTION

PATENT NO. : 5,796,106
DATED : Aug. 18, 1998
INVENTOR(S) : Noack

It is certified that error appears in the above-identified patent and that said Letters Patent is hereby corrected as shown below:

The title page should be deleted to appear as per attached title page.

Please delete drawing sheet 3 of 4 and substitute drawing sheet 3 of 4 as per attached.

Signed and Sealed this

Eighth Day of June, 1999

Attest:

Q. TODD DICKINSON

*Attesting Officer* *Acting Commissioner of Patents and Trademarks*

US005796106A

United States Patent [19]

Noack

[11] Patent Number: 5,796,106
[45] Date of Patent: Aug. 18, 1998

[54] ICE AND LIQUID DETECTOR

[76] Inventor: Raymond James Noack, P.O. Box 898, Springwood, Queensland, 4127, Australia

[21] Appl. No.: 765,236

[22] PCT Filed: Jun. 13, 1995

[86] PCT No.: PCT/AU95/00345

§ 371 Date: Dec. 18, 1996

§ 102(e) Date: Dec. 18, 1996

[87] PCT Pub. No.: WO95/35493

PCT Pub. Date: Dec. 28, 1995

[30] Foreign Application Priority Data

Jun. 20, 1994 [AU] Australia .............................. PM 6319

[51] Int. Cl.[6] .......................... G01N 21/88; G01N 21/01

[52] U.S. Cl. .................................. 250/341.8; 250/341.1; 15/DIG. 15

[58] Field of Search ............................ 250/341.1, 341.8, 250/339.11; 15/DIG. 15

[56] References Cited

U.S. PATENT DOCUMENTS

| | | | |
|---|---|---|---|
| 3,947,131 | 3/1976 | Karl | 250/341.8 X |
| 4,620,141 | 10/1986 | McCumber et al | 15/DIG. 15 X |
| 5,414,257 | 5/1995 | Stanton | 250/341.8 X |

FOREIGN PATENT DOCUMENTS

| | | | |
|---|---|---|---|
| 4312590 | 10/1993 | Germany | 250/341.8 |

*Primary Examiner*—Edward J. Glick
*Attorney, Agent, or Firm*—Mathews, Collins, Shepherd & Gould, P.A.

[57] ABSTRACT

A detector for detecting the presence of ice, water, mist, frost or other solids or liquids on a sensing surface is provided. The sensing surface is provided by a medium substantially transparent to electromagnetic radiation and solids or liquids are deposited on the surface. A transmitter directs radiation onto the surface and a receiver is responsive to radiation reflected from the surface. A discriminator circuit receivers an output from the receiver and provides an output indicative of whether a solid or a liquid is present on the surface.

9 Claims, 4 Drawing Sheets